United States Patent [19]

Taniguchi et al.

[11] 4,103,776
[45] Aug. 1, 1978

[54] INSPECTION MACHINE FOR FUEL PELLETS

[75] Inventors: Tadashi Taniguchi, Kawagoe; Takeshi Miyaoka, Sayama; Daiji Hagino, Tokorozawa; Ken-ichi Matsumoto, Naka; Kazuo Sakamoto, Higashi-Ibaragi; Akira Matsuda, Nakaminato; Toshio Shishido, Naka, all of Japan

[73] Assignees: Citizen Watch Company Limited; Doryokuro Kakunenryo Kaihatsu Jigyodan, both of Tokyo, Japan

[21] Appl. No.: 722,241

[22] Filed: Sep. 10, 1976

[30] Foreign Application Priority Data

Sep. 16, 1975 [JP] Japan .................. 50-111870

[51] Int. Cl.² .................................. B07C 1/10
[52] U.S. Cl. ........................... 209/73; 209/82; 209/75
[58] Field of Search .............. 73/37, 37.5, 37.6, 37.8; 209/80, 82, 73, 74

[56] References Cited

U.S. PATENT DOCUMENTS

| 2,421,484 | 6/1947 | Diamond | 209/82 |
| 2,651,412 | 9/1953 | Aller | 73/37.6 X |
| 3,895,516 | 7/1975 | Swartz | 73/37.6 |

Primary Examiner—Allen N. Knowles
Attorney, Agent, or Firm—Frank J. Jordan

[57] ABSTRACT

An inspection machine for detecting flaws in the surface of cylindrical fuel pellets, which comprises a pellet infeed section for successively transporting pellets to be inspected, a conveyer section for successively conveying delivered pellets to a plurality of inspection points, a plurality of inspection stations for detecting, at each inspection point, flaws at the corners, peripheral surface and end faces of the pellets by utilizing variations in back pressure prevailing in a sensor caused by the contact of an air stream with said flaws, an unacceptable pellet rejection station for rejecting pellets assessed to be unacceptable at any inspection station, and an acceptable pellet outfeed section for successively collecting pellets assessed as being acceptable.

8 Claims, 15 Drawing Figures

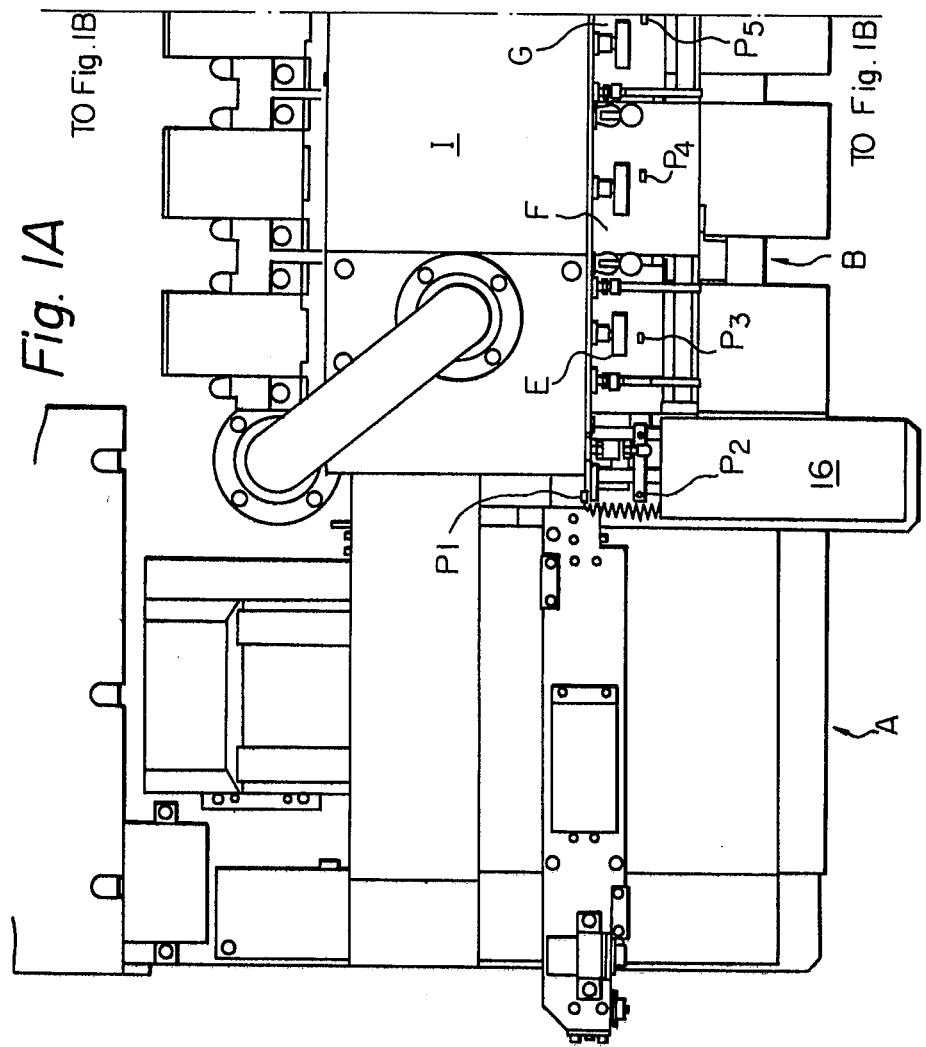

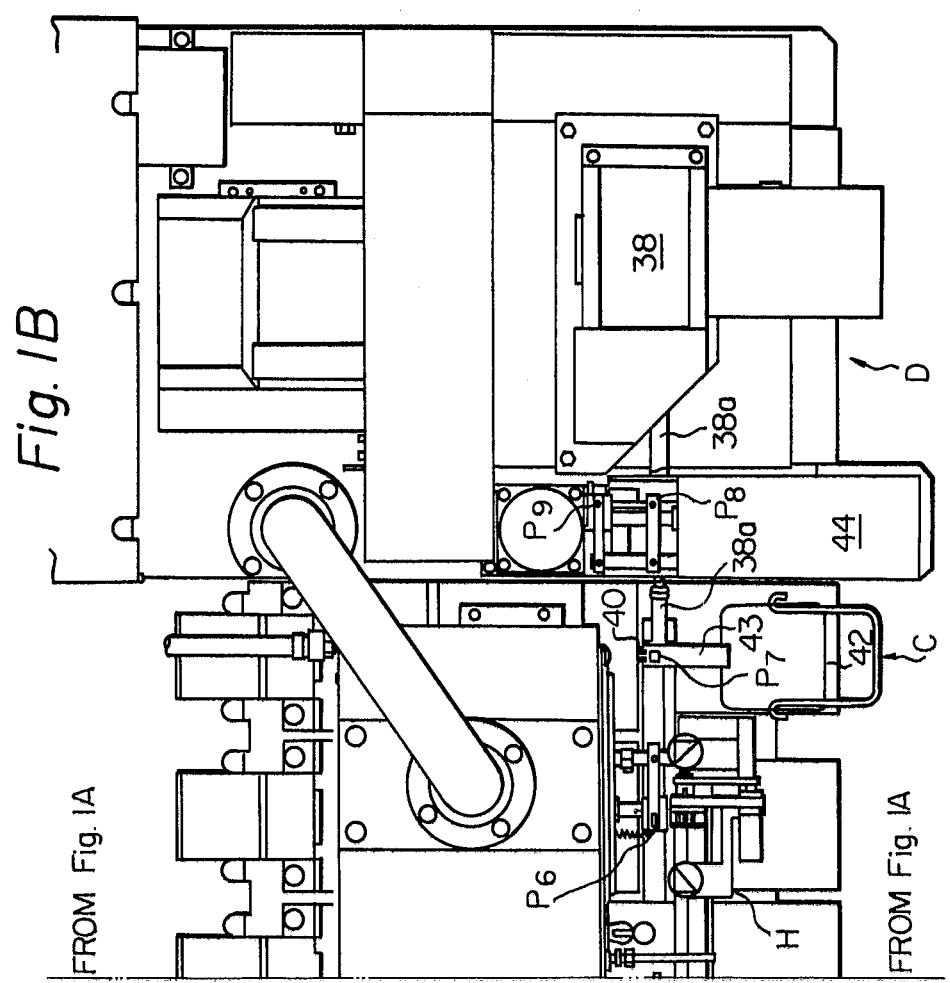

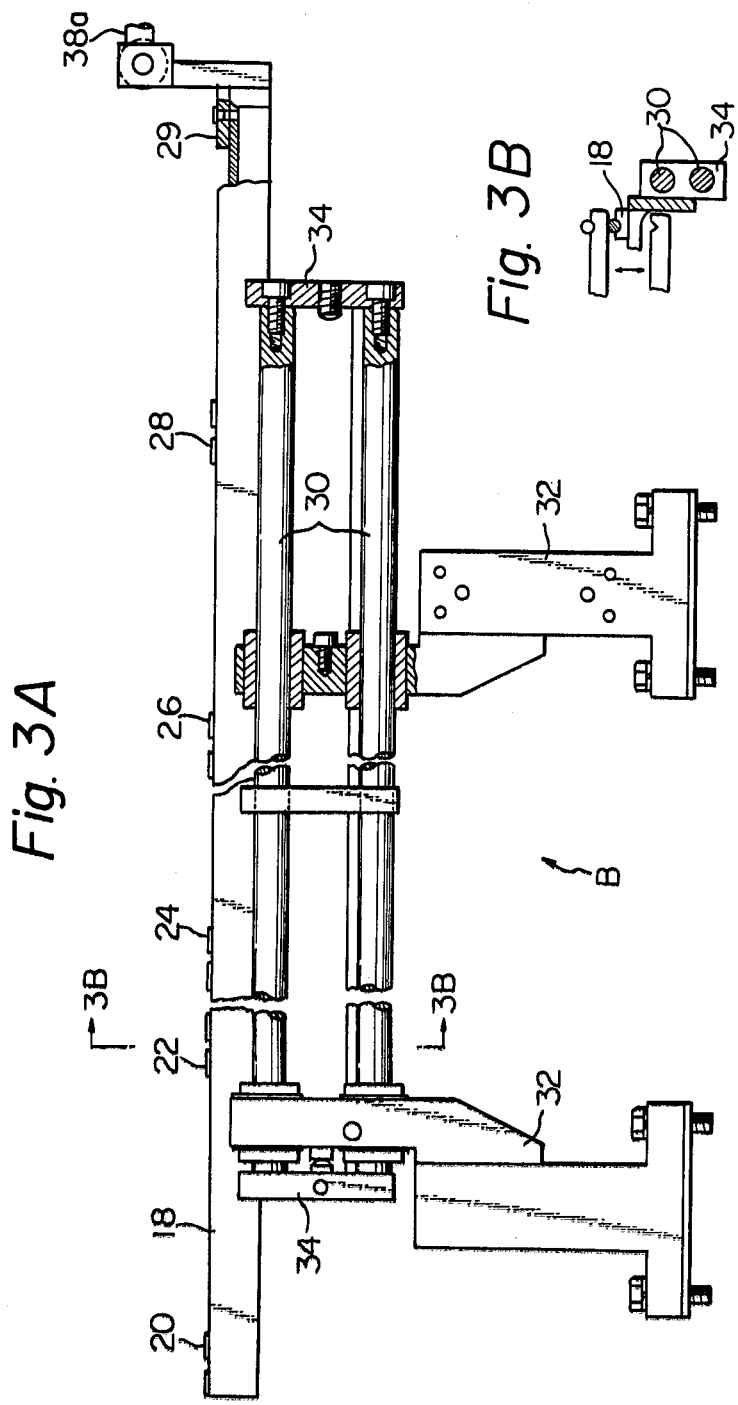

INSPECTION MACHINE FOR FUEL PELLETS

This invention relates to inspection machines for cylindrical pellets and, more particularly, to an inspection machine which detects flaws such as chips and cracks in the surface of cylindrical fuel pellets.

In industry an increasingly large number of products are assuming a cylindrical shape and detection of the surface conditions of these products is all important. For example, fuel pellets for Fast Breeder Reactors and mixed-oxide fuel pellets such as $PuO_2$-$UO_2$ for Advanced Thermal Converter Reactors are cylindrical sintered bodies with flat end-faces. These finished products when undergoing inspection are checked for cracks, chips and fissures and any pellet exhibiting such flaws must be set apart when certain standards cannot be met.

Since fuel pellets are radioactive, mechanization of the inspection process is highly desirable in view of safety especially in the case of occupational radiation exposure control in mixed-oxide fuel fabrication plant. Fuel pins fabricated by stacking a number of fuel pellets within a tubular clad cannot function properly under the high temperatures which exist in a reactor if the pellets are flawed in any way. Damaged pellets have a deleterious effect upon the clad itself which can be a hindrance to smooth reactor operation. It is thus necessary that the surface of such pellets be closely inspected and that only those components that fall with predetermined standards be assessed as acceptable.

In prior art, inspection of the flaws in the cylindrical fuel pellets have been usually performed by simple visual checks, which are time consuming and present undesirable effect on human bodies. Another drawback resides in that an accurate inspection of the flaws can not reliably performed.

It is, therefore, an object of the present invention to provide an inspection machine capable of automatically detecting flaws in the end-faces, corners and the cylindrical periphery of cylindrical bodies. According to the machine as herein disclosed inspection is performed irrespective of the physical properties of the product to be inspected and no electrical means are used to thus provide greater safety.

It is another object of the present invention to provide an inspection machine employing an improved cylindrical inspection station adapted to automatically detect the cylindrical periphery of cylindrical bodies.

It is another object of the present invention to provide an inspection machine suited for inspection of cylindrical fuel pellets for an advanced thermal converter reactor.

It is a further object of the present invention to provide an inspection machine which is simple in construction, easy to repair and highly reliable in operation.

In the accompanying drawings, in which:

FIGS. 1A and 1B show a plan view of a preferred embodiment of an inspection machine according to the present invention;

FIG. 3A is an enlarged diagrammatic view of a conveyer section forming part of the inspection machine shown in FIGS. 1A and 1B;

FIG. 3B is a cross sectional view of FIG. 3A taken along the line 3B-3B;

Figure 2A:
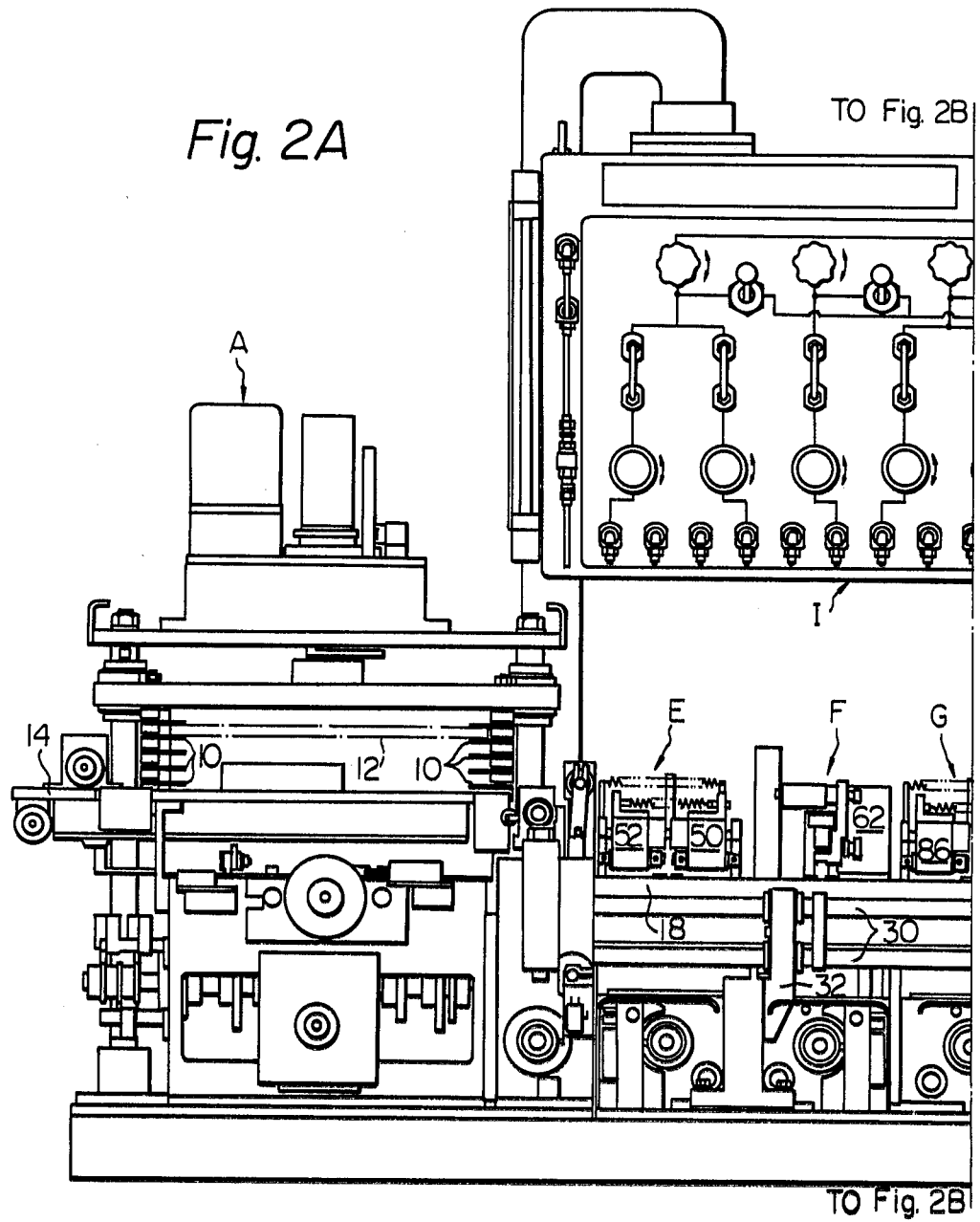
FIGS. 2A and 2B show a front view of the inspection machine shown in FIG. 1.
Figure 2B:
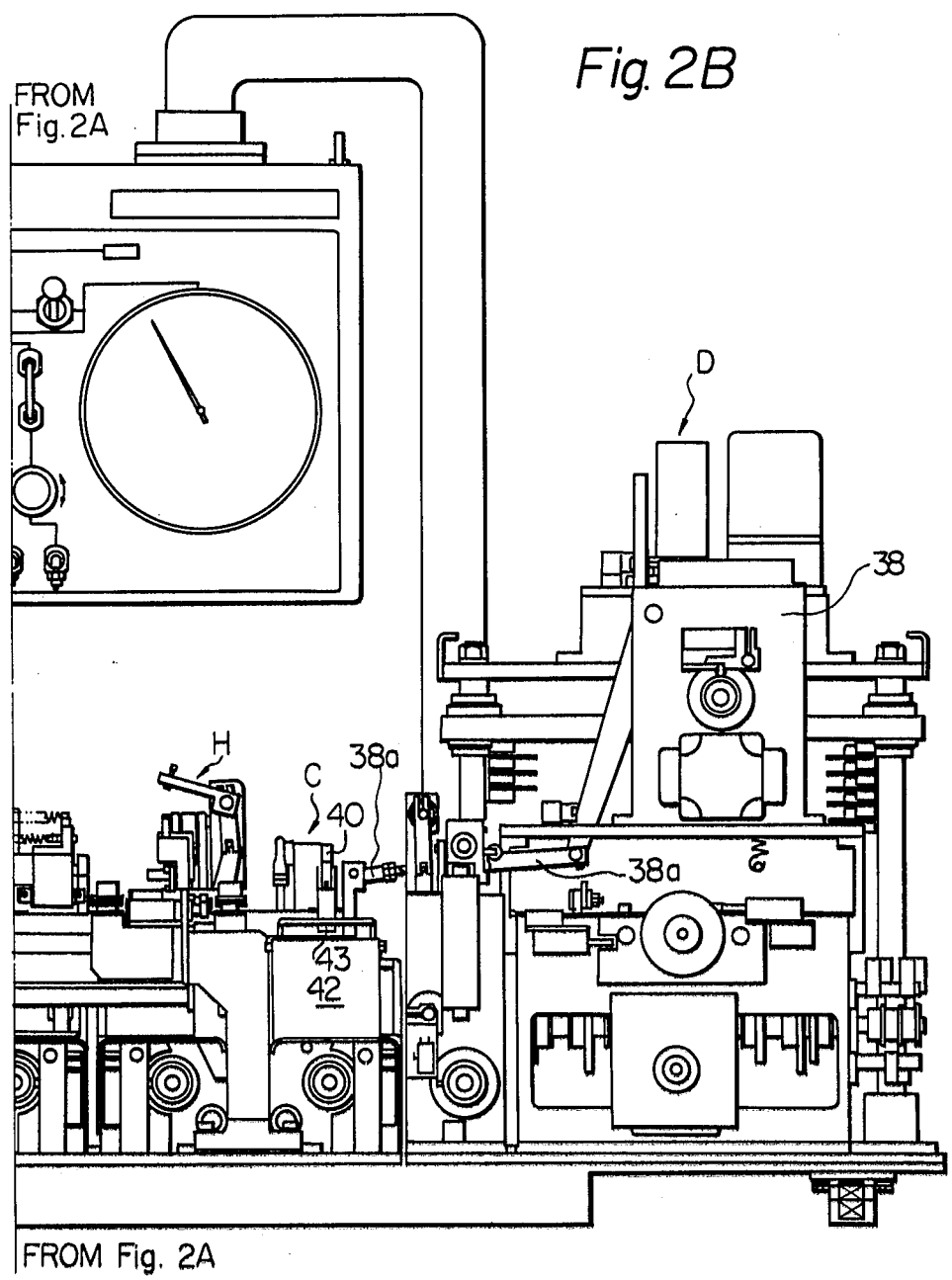

Referring now to FIGS. 1 and 2, there is shown a preferred embodiment of an automatic inspection machine for fuel pellets according to the present invention. The automatic inspection machine generally includes a pellet infeed section A for successively transporting in small increments and at a given timing cylindrical fuel pellets to be inspected, a conveyer section B for successively conveying the pellets so delivered, an unacceptable pellet reject station C for rejecting unacceptable pellets which have reached the terminus of conveyer section B, and an outfeed section D for accommodating pellets found to be acceptable. A corner inspection station E, a cylindrical inspection station F, and end-face inspection station G and a visual inspection station H are arranged along the path of the conveyer section B. An air feed unit I is disposed above respective inspection stations E through G for the purpose of supplying air at a constant prescribed pressure.

Pellet infeed section A includes a plurality of supporting members 10 which support a number of vertically arranged trays 12, and an actuating mechanism adapted to move the supporting members 10 in a vertical and horizontal manner such that a given row of pellets from a given tray 12 are moved to and maintained in a prescribed supply line. A row of pellets at the head of the supply line is pushed by a plunger mechanism 14 through a distance equal to the length of one pellet such that a pellet at the foremost end of the line is delivered to a first position P1. The pellet which has thus arrived at position P1 is then carried to and held at a second position P2 by an infeed unit 16.

Conveyer section B, as may be seen in more detail in FIG. 3A, includes a narrow elongated transfer beam 18 composed of sit carriers 20, 22, 24, 26, 28 and 29 which are spaced at prescribed intervals. Longitudinal reciprocation of transfer beam 18 through a prescribed distance or stroke equivalent to the interval between adjacent carriers is accomplished by a pair of longitudinally movable rods 30 supported between a pair of supporting columns 32. Transfer beam 18 is mounted to both ends of rods 30 by way of connecting members 34, and the foremost end of rod 38a of driving device 38 is pivotally connected to one end of transfer beam 18. Driving device 38 through means of a crank or the like is operable to reciprocate rod 38a in response to which transfer beam 18 will reciprocate in a longitudinal manner. Pellets carried on each of the carriers 20 - 29 are picked up from the transfer beam 18 by a lifting mechanism while the transfer beam is returning from the right side of its stroke to the left side. Once the transfer beam has reached the left side of its stroke, the pellets are again placed on the next carrier and carried to the subsequent inspection station. As a result, pellets are successively forwarded from the second position P2 to the third through eighth positions P3-P8.

Pellets which arrive at position P7 and are found to be unacceptable are ejected in a transverse direction by fork 40 located in pellet reject station C and are then collected in bucket 42 after passing through chute 43. If the pellets are acceptable, however, outfeed unit 44 delivers them from an eighth position P8 to a ninth position P9 for collection in a tray located at the outfeed section D. A description of this section will be omitted as it is essentially identical in structure to the pellet infeed section A.

Figure 4:
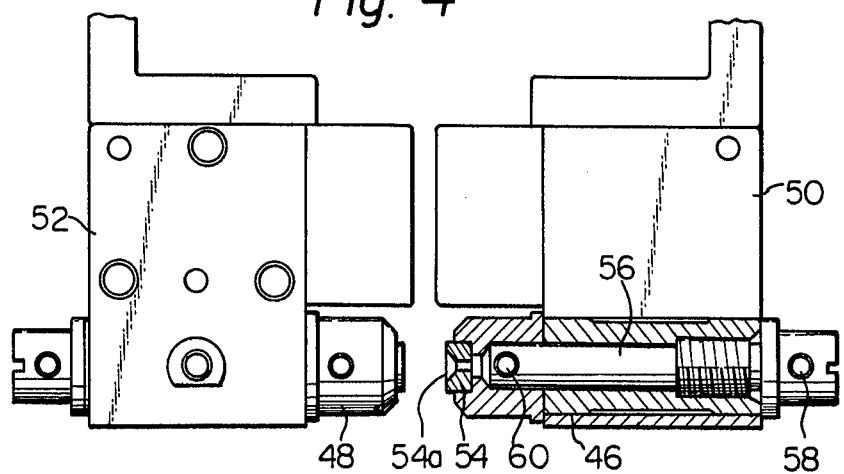
FIG. 4 is an enlarged fragmentary view, partially in cross section, of a corner inspection station forming part of the inspection machine.

Pellets which have arrived at position P3 are delivered to corner inspection station E by means of the lifting mechanism shown in FIG. 3B. As shown in FIG. 4, inspection station E comprises sensors 46 and 48 respectively mounted to a pair of blocks 50 and 52 which are movable so as to be movable toward and away from each other. Sensor 46 is provided at one end with a tip 54 having an aperture 54a the inner peripheral surface of which is tapered. Aperture 54a communicates with an air chamber 56 supplied with air at constant pressure as provided by air supply unit I via an air hose (not shown) and a connector 58. The pressure within air chamber 56 is tapped via another hose (not shown) and a connector 60 so that it may be measured by a pressure sensor employing pressure-electric converter for converting the sensed pressure into electrical information. Sensor 48 is identically constructed and so a detailed description is omitted.

Inspection for corner chips is performed by holding a pellet between sensors 46 and 48 is such a manner that the end face of the pellet seals off the aperture 54a at the inner periphery thereof, whereby air under a constant pressure may be delivered to air chamber 56. If the corner of the pellet is unflawed, there will be no leakage of air across the end face since the corner will seal aperture 54a along its inner periphery. However, should any flaws be present, air within chamber 56 will escape and the back pressure within the chamber will drop in proportion to the cross-section area of the flaw. A drop in the back pressure will be detected by the pressure sensor through connector 60. In this way it is possible to detect the size of a flaw should one exist in either corner of the pellet. If the drop in pressure indicative of the flaw size should exceed a certain pre-set value, a signal indicative of pellet unacceptability is retained by a suitable electrical memory circuit.

A pellet which has undergone the corner inspection is once again dropped to position P3 by means of the lifting mechanism. Transfer beam 18 which has returned to the leftward side of its stroke during pellet inspection then begins to move to the right after the pellet has arrived at position P3; the pellet at P3 is thus carried to position P4 which, after it arrives, is lifted by a lifting mechanism in order to deliver it to cylindrical inspection station F.

Figure 5:
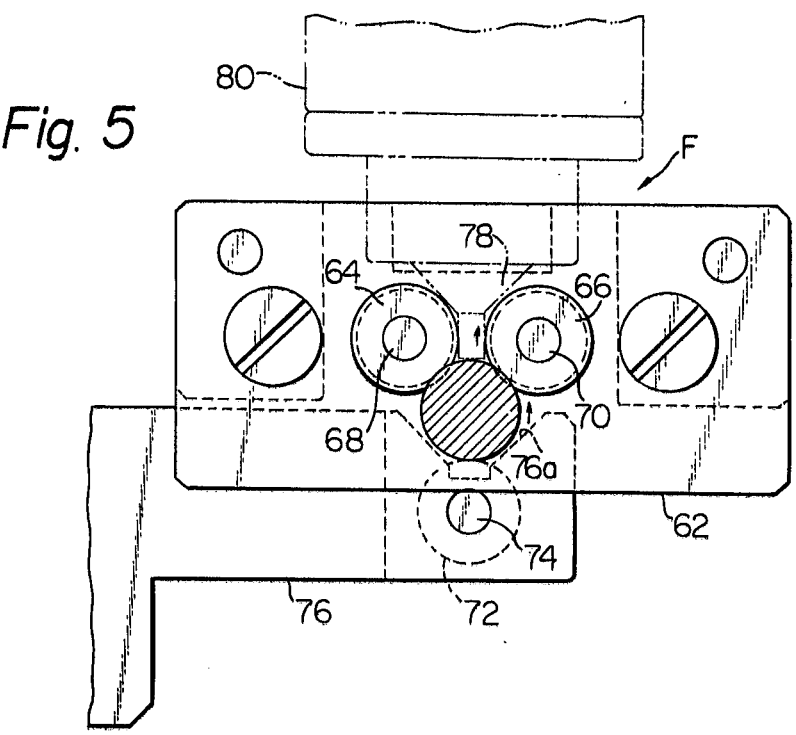
FIG. 5 is an enlarged fragmentary view of a cylindrical inspection station forming part of the inspection machine.

The structure of the cylindrical inspection station is shown in FIG. 5. Here reference numeral 62 denotes a supporting block which axially supports a pair of rollers 64 and 66 through the intermediary of mutually parallel shafts 68 and 70. On the other hand, a roller 72 is rotatably mounted on shaft 74 supported by arm 76 of the lifting mechanism. A portion of the outer peripheral surface of roller 72 is positioned at the lowermost portion of a V-shaped groove 76a formed at the end of arm 76 in order to rotatably support the pellet. The outer peripheral surface of a pellet to be inspected is positioned so as to contact the surface of roller 72. When arm 76 has been elevated to the maximum extent, the outer peripheral surface of the pellet comes into contact with each of the rollers 64, 66 and 72 and the pellet is then held at a predetermined position. Although roller 72 is freely rotatable, rollers 64 and 66 are rotated in a given direction and at the same speed by means of a driving mechanism (not shown). As a result, the pellet is caused to rotate at the same peripheral speed and in the same direction. Air under pressure is ejected onto the surface of the pellet by means of nozzle 78 disposed between rollers 64 and 66. If the peripheral surface of the pellet is unflawed, the quantity of air escaping from the above-defined space in the vicinity of nozzle 78 will attain a given minimum value. The quantity of air escaping will, however, increase in cases where the pellet is flawed. Accordingly, if the increase in the amount of air out-flow (obtained as a drop in the back pressure of the nozzle) is calculated during the time it takes for one revolution of the pellet, then a signal indicative of the over-all size of the flaw can be obtained. If this value should exceed that of one predetermined, a signal indicative of the unacceptability of this pellet is retained by the above-mentioned memory circuit.

Figure 6A:
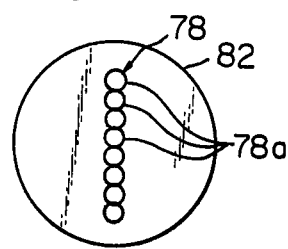
FIGS. 6a, 6b, 7a, 7b, 8a and 8b are enlarged fragmentary views showing preferred examples of a nozzle forming part of the cylindrical inspection station shown in FIG. 5.
Figure 6B:
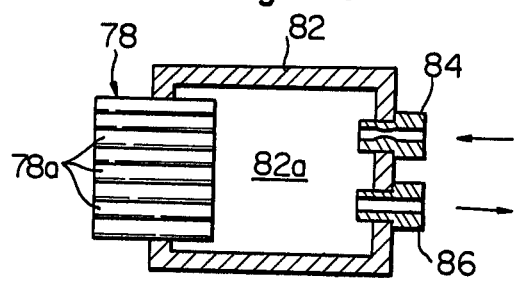

FIGS. 6a and 6b show a preferred example of nozzle 78 forming part of the cylindrical inspection station F shown in FIG. 5. In this preferred example, nozzle 78 comprises a plurality of thin wall pipes 78a which are continuously arranged in parallel. The thin wall pipes 78a communicate with air chamber 82a formed in casing 82, to which air inlet 84 and air outlet 86 are connected. Air inlet 84 is connected to air supply unit I so as to supply air under pressure into air chamber 82a. The pressure in air chamber 82a is tapped via outlet 86 so that it may be measured in sensor 80 employing means for converting the sensed pressure into electrical information. As best shown in FIG. 6a, each pipe 78a has a cylindrical shape in cross section to provide a larger sensing distance. Also, the outer periphery of nozzle 78 is larger in length than that of a prior art nozzle formed in a rectangular shape, providing increased sensing reliability. Since, further, each pipe 78a has a thin wall thickness, it is possible to detect small flaws in the pellet in a highly reliable manner. Another advantage is that nozzle 78 has a greater flow resistance provided by a plurality of long pipes 78a to reduce air consumption to a minimum value.

Figure 7A:
Figure 7B:
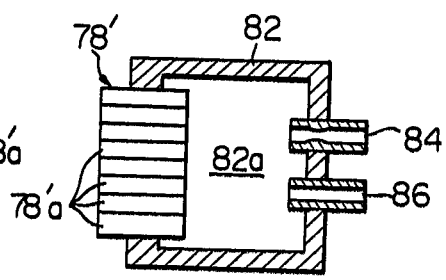

A modified form of the nozzle is shown in FIGS. 7a and 7b with like parts bearing like reference numerals as those used in FIGS. 6a and 6b except that a single suffix (') is added to those which are modified. The illustrated example of FIGS. 7a and 7b differs from that of FIGS. 6a and 6b only in that each pipe 78'a has a rectangular shape in cross section as best shown in FIG. 7a. This configuration provides the same effect as the nozzle 78 shown in FIGS. 6a and 6b.

Figure 8A:
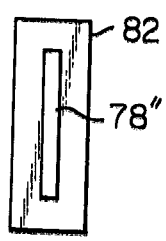
Figure 8B:
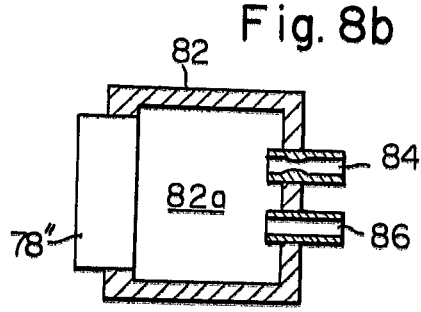

FIGS. 8a and 8b show another modified form of the nozzle shown in FIG. 6. In this example, nozzle 78" comprises an elongated slit instead of a plurality of pipes 78a. Nozzle 78" will operate in the same manner as that of FIGS. 6a and 6b and so a detailed description is omitted.

Figure 9:
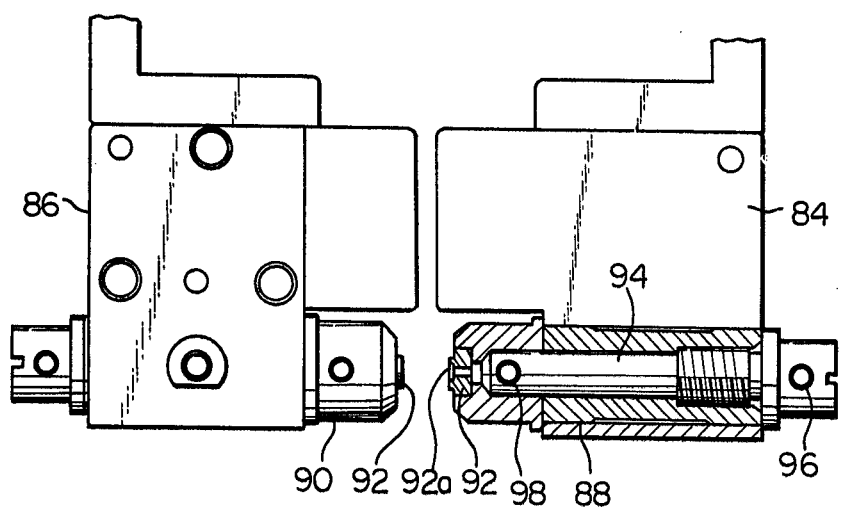
FIG. 9 is an enlarged fragmentary view of an end face inspection station forming part of the inspection machine.

A pellet which has undergone the cylindrical inspection is next returned to position P4, transferred by transfer beam 18 to position P5 and then delivered to end-face inspection station G by the lifting mechanism. End-face inspection station G, as shown in FIG. 9, is composed of a pair of movable blocks 84 and 86 and their associated sensors 88 and 90, each of which includes a tip 92 having an aperture 92a, an air chamber 94 and connecters 96 and 98. It will be seen in comparison with the corner inspection station E of FIG. 4 that this end-face inspection station G is substantially identical in structure. Points of differences are to be found in that the opening of aperture 92a is slightly smaller in diameter than the end-face of the pellet, and in the fact that during inspection an extremely small gap exists between the end-face of tip 92 and the end-face of the pellet. When the end-face of the pellet is disposed to face tip 92 across a slight gap and air is ejected from aperture 92a, subtle differences develop in the flow of air across the end face of the pellet when comparing cases where the surface is extremely smooth, indicating the absence of flaws, to cases where depressions exist due to irregularities in form. These differences appear as differences in back pressure in the back of aperture 92a. Accordingly, it is possible to detect the absence or presence of flaws in the end face by detecting the back pressure. When the detected value exceeds a predetermined value, a signal indicative of an unacceptable pellet is retained in a memory circuit.

A pellet which has passed through this inspection is returned to position P5 and transferred onto position P6 where it is lifted to the visual inspection station H by the lifting mechanism. The visual inspection station H includes means for slowly rotating the pellet about its center axis, a television camera for taking pictures, and a television monitor for observing the TV picture. An optical system may preferably be employed in which prisms or mirrors are used to obtain pictures of the end faces and peripheral surface of the pellet through the use of only one camera. The picture provided by the TV monitor is viewed with the naked eye as a final check upon completion of the proceeding inspections and can be used when necessary to check for contamination or other such conditions. For a fully automated system, the television screen can be provided with a suitable mask through which the illumination of the picture can be measured and unacceptable pellets discovered. It is also possible to perform an electrical analysis of the television picture by employing electrical output signals which can be made to conform to the light and dark tones and the contrast of the picture. Since either or all of these systems may be employed, a further description of the visual inspection station will be omitted.

Pellets assessed to be unacceptable at any of the inspection stations E-H are, when they reach position P7, ejected by fork 40 operable in response to a command from a memory circuit. Only these pellets which are acceptable reach outfeed section D after having passed through positions P8 and P9.

It is thus apparent from the above explanation that the present invention makes it possible to automatically detect the size of flaws which may exist in the corners, on the peripheral surface or in the end faces of pellets, so that unacceptable pellets can be reliably detected. Furthermore, inspection remotely performed using changes in air pressure to determine the condition of the pellets assures greater safety and reduces the possibility of damage being inflicted upon the pellets by the measuring devices themselves.

Another feature of the present embodiment resides in the fact that the pellet infeed section A, the conveyor section B, the unacceptable pellet reject station C, the outfeed section D, the inspection stations E - H and the air feed unit I are separately formed from each other as units which can be dismounted and readily rejoined to allow easy repair of the unit or units in which failure occurs. In addition, as large external forces are not applied upon the pellets during conveyance and inspection, there is no fear that pellets will sustain any damage.

It will now be appreciated from the foregoing description that a sensor incorporated in a cylindrical inspection station of the present invention makes it possible to accurately detect the flaws in the peripheral surfaces of the pellets which have varying diameter portions, tapered portions or irregur surfaces, etc., such as sintered fuel pellets, for an advanced thermal converter reactor, of which outer peripheries are not finished with grinding work.

While the present invention has been shown and described with reference to particular embodiments by way of example, it should be noted that various other changes or modifications may be made without departing from the scope of the present invention.

What is claimed is:

1. A cylindrical inspection station for an inspection machine adapted to detect the surface of cylindrical pellets, which inspection machine has a supporting block comprising:
   a pair of rollers rotatably supported on shafts mounted in parallel to said supporting block;
   a lifting mechanism including an arm formed with a groove to support each of said pellets;
   an additional roller rotatably supported by said arm for rotatably supporting said each of the pellets in said groove;
   said arm being movable to a position to cause an outer surface of said each of the pellets to come into contact with each of said rollers of said pair of rollers such that said each of the pellets is held at a predetermined position; and
   means for detecting flaws in an outer periphery of said each of the pellets by utilizing changes in pressure caused by the contact of an air stream with said flaws.

2. A cylindrical inspection station according to claim 1, in which said detecting means comprises a source of air under pressure, a nozzle communicating with said source of said under pressure for ejecting air under pressure onto the outer periphery of said each of the pellets at a position between said pair of rollers, and a sensor communicating with said nozzle for detecting said changes in pressure caused by the contact of said air stream with said flaws.

3. A cylindrical inspection station according to claim 2, in which said nozzle comprises a plurality of thin wall pipes disposed in parallel with each other.

4. A cylindrical inspection station according to claim 3, in which each of said pipes has a circular shape in cross section.

5. A cylindrical inspection station according to claim 3, in which each of said pipes has a rectangular shape in cross section.

6. A cylindrical inspection station according to claim 2, in which said nozzle comprises an elongated slit.

7. An inspection machine for detecting flaws in the surface of cylindrical pellets, comprising:
   pellet infeed means for successively transporting pellets to be inspected;
   conveyer means for successively conveying delivered pellets to a plurality of inspection points;
   a plurality of inspection means for detecting, at each inspection point, flaws at the corners, peripheral surface and end faces of said pellets by utilizing changes in pressure caused by the contact of an air stream with said flaws;

unacceptable pellet rejection means for rejecting pellets assessed to be unacceptable at any inspection station; and acceptable pellet outfeed means for successively collecting pellets assessed as being acceptable;

said plurality of inspection means including a pair of rollers rotatably supported on shafts mounted in parallel to a supporting block of said machine, a lifting mechanism including an arm formed with a groove to support each of said pellets to be detected, an additional rollers rotatably supported on said arm for rotatably supporting said each of said pellets in said groove, and means for ejecting air under pressure onto the peripheral surface of said each of said pellets at a position between said pair of rollers to detect flaws in the outer periphery of said each of said pellets.

8. An inspection machine according to claim 7, in which said pellet infeed means, said conveyer means, said plurality of inspection means, said unacceptable pellet rejection means and said acceptable pellet outfeed are formed as units, respectively.

* * * * *